(12) United States Patent
Hine et al.

(10) Patent No.: US 7,076,309 B2
(45) Date of Patent: Jul. 11, 2006

(54) APPARATUS AND METHOD FOR FIXEDLY ENGAGING AN ELECTRICAL LEAD

(75) Inventors: Douglas S. Hine, White Bear Lake, MN (US); John L. Sommer, Coon Rapids, MN (US); Vicki L. Bjorklund, Maple Grove, MN (US); Bernhard Kupper, Dusseldorf (DE)

(73) Assignee: Medtronic, Inc., Minneapolis, MN (US)

(*) Notice: Subject to any disclaimer, the term of this patent is extended or adjusted under 35 U.S.C. 154(b) by 519 days.

(21) Appl. No.: 10/137,466

(22) Filed: Apr. 30, 2002

(65) Prior Publication Data

US 2003/0204234 A1    Oct. 30, 2003

(51) Int. Cl.
*A61N 1/05*    (2006.01)
*A61B 5/042*   (2006.01)

(52) U.S. Cl. ............... 607/128; 607/127; 607/131; 600/375

(58) Field of Classification Search ........ 607/126–128, 607/133, 130, 131; 600/380, 381, 375, 386; 606/107–109
See application file for complete search history.

(56) References Cited

U.S. PATENT DOCUMENTS

| | | | |
|---|---|---|---|
| 3,981,309 A * | 9/1976 | Cannon | 607/121 |
| 4,957,118 A | 9/1990 | Erlebacher | |
| 5,170,802 A | 12/1992 | Mehra | |
| 5,224,491 A | 7/1993 | Mehra | |
| 5,239,999 A * | 8/1993 | Imran | 600/374 |
| 5,259,395 A * | 11/1993 | Li | 607/131 |
| 5,387,233 A | 2/1995 | Alferness et al. | |
| 5,423,772 A | 6/1995 | Lurie et al. | |
| 5,683,445 A | 11/1997 | Swoyer | |
| 5,683,447 A * | 11/1997 | Bush et al. | 607/126 |
| 5,693,081 A | 12/1997 | Fain et al. | |
| 5,991,668 A | 11/1999 | Leinders et al. | |
| 6,006,122 A | 12/1999 | Smits | |
| 6,322,559 B1 * | 11/2001 | Daulton et al. | 606/41 |
| 6,711,443 B1 * | 3/2004 | Osypka | 607/122 |

FOREIGN PATENT DOCUMENTS

| | | |
|---|---|---|
| EP | 0004967 A2 | 11/1978 |
| EP | 0393265 A1 | 10/1990 |
| EP | 0571985 A2 | 12/1993 |
| SE | EP0570712 * | 11/1993 |

* cited by examiner

*Primary Examiner*—Jeffrey R. Jastrzab
*Assistant Examiner*—John D. Alexander
(74) *Attorney, Agent, or Firm*—Paul H. McDowall; Michael C. Soldner; Girma Wolde-Michael (57) ABSTRACT

An electrical lead includes an elongate body having a proximal end and a fixation member joined to the elongate body and distally disposed from the proximal end of the elongate body, wherein the fixation member is capable of being extended from and retracted toward the elongate body. A method includes advancing an electrical lead into vasculature and extending a fixation member from the body of the electrical lead to fixedly engage the electrical lead within the vasculature. The method may further include retracting the fixation member toward the body of the electrical lead to unengage the electrical lead within the vasculature and retracting the electrical lead from the vasculature.

10 Claims, 11 Drawing Sheets

APPARATUS AND METHOD FOR FIXEDLY ENGAGING AN ELECTRICAL LEAD

FIELD OF THE INVENTION

This invention generally relates to an implantable medical device and, more particularly, to an apparatus and method for engaging an electrical lead of an implantable medical device.

DESCRIPTION OF THE RELATED ART

Since the introduction of the first implantable pacemakers in the 1960s, there have been considerable advancements in both the fields of electronics and medicine, such that there is presently a wide assortment of commercially available implantable medical devices. The class of implantable medical devices now includes therapeutic and diagnostic devices, such as pacemakers, cardioverters, defibrillators, neural stimulators, and drug administering devices, among others. Today's state-of-the-art implantable medical devices are vastly more sophisticated and complex than their early counterparts, and are capable of performing significantly more complex tasks. The therapeutic benefits of such devices have been well proven.

Modern electrical therapeutic and/or diagnostic devices for the heart require a reliable electrical connection between the device and a region of the heart. Typically, a "lead" is used to electrically couple the therapeutic and/or diagnostic device to a portion of the heart. One type of commonly used implantable lead is a transvenous lead, which is generally positioned through the venous system to a location proximate the heart. A proximal end of the transvenous lead is typically connected to the electrical therapeutic and/or diagnostic device, which may be implanted. Such leads normally take the form of a long, flexible, insulated conductor. Among the many advantages of transvenous leads is to provide an electrical contact with the heart without physically exposing the heart itself, i.e., major thoracic surgery is not required.

In certain circumstances, it is particularly advantageous to finally position such leads within vasculature proximate the heart, such as within a coronary sinus, a coronary vein, or the like. Once optimally positioned, it is desirable for the lead, and thus the electrode or electrodes that are part of the lead, to remain in a set position. Movement of the electrode or electrodes relative to the portion of the heart to be affected by electrical stimuli emitted from the electrode or electrodes may result in the stimuli having an inadequate effect on the heart. Further, if the electrode or electrodes are allowed to move, another portion of the heart may inadvertently and undesirably be stimulated.

Leads have been developed that include features for holding the leads in place within vasculature. For example, such a lead may have a helix shape that generally conforms to the inside dimension of the vessel. Other such leads may have a tine or other engaging feature extending therefrom that may engage the wall of the vessel to inhibit movement of the lead within the vessel. However, these holding features are positionally static and may inhibit the removal of the leads from which they extend, making removal of the lead from the vessel difficult.

The present invention is directed to reducing the effects of one or more of the problems set forth above.

SUMMARY OF THE INVENTION

In one aspect of the present invention, a lead of an implantable medical device includes an elongate body having a proximal end, and a fixation member joined to the elongate body. The fixation member is distally disposed from the proximal end of the elongate body, and is capable of being extended outward from and retracted inward toward the elongate body.

In another aspect of the present invention, a lead of an implantable medical device includes means for fixedly engaging the lead within vasculature, and means for selectively rotating the engaging means between an outward extended position to fixedly engage the lead within the vasculature and an inward retracted position to disengage the lead from the vasculature to reposition the lead within the vasculature.

In yet another aspect of the present invention, an implantable medical device for implantation within a patient includes a housing portion that generates an electrical stimulus. A lead is coupled to the housing portion for insertion within vasculature of the patient to transmit the electrical stimulus to the patient and to sense physiological conditions of the patient. A fixation member positioned along the lead is rotated from a closed, retracted position to an open extended position to fixedly engage the lead during positioning of the lead within the vasculature, and is rotated from the open extended position to the closed retracted position to disengage the lead during repositioning of the lead within the vasculature.

BRIEF DESCRIPTION OF THE DRAWINGS

The features of the present invention which are believed to be novel are set forth with particularity in the appended claims. The invention, together with further objects and advantages thereof, may best be understood by making reference to the following description, taken in conjunction with the accompanying drawings, in the several figures of which like reference numerals identify like elements, and wherein:

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

Figure 1:
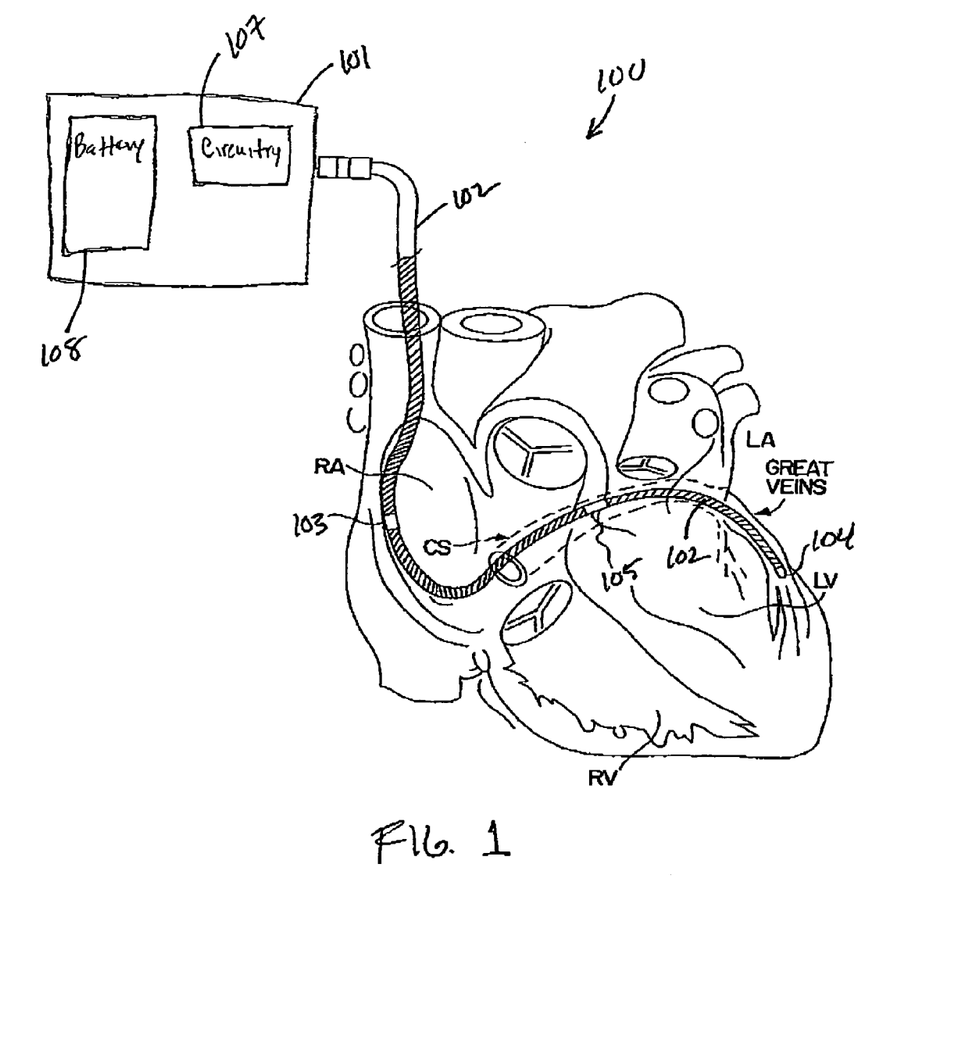
FIG. 1 is a simplified schematic diagram of an implantable medical device according to the present invention.

FIG. 1 is a schematic diagram of an implantable medical device according to the present invention. As illustrated in FIG. 1, an implantable medical device 100 according to the present invention includes a lead 102 attachable to and extending from an implantable medical device housing portion 101 to a tip electrode 104. Housing portion 101 includes circuitry 107 and a battery 108 for generating an electrical stimulus through lead 102. Lead 102 may also include one or more electrodes 103, 105 that, in addition to tip electrode 104, are used transmit the electrical stimulus from housing portion 101 to stimulate a tissue of a body and/or sense one or more physiological conditions in the tissue once lead 102 is placed within the great veins of the coronary sinus (CS), for example. Examples of such implantable medical devices are implantable coronary pacing devices, pulse generators, defibrillators, neural stimulation devices, electrogram devices, and the like. Generally, these devices operate by monitoring one or more conditions in the tissue and/or by delivering electrical stimuli to the tissue via the lead or leads. For example, such devices may be used to sense cardiac activity, to deliver electrical pacing stimuli to a portion or portions of a heart, to deliver electrical defibrillating stimuli to a portion or portions of the heart, to deliver electrical stimuli to a nerve, to deliver electrical stimuli to a portion or portions of a nerve bundle, or to deliver electrical stimuli to a portion or portions of a brain. While the description provided herein is directed to an implantable medical device used in a coronary setting, the present invention encompasses any implantable medical device, such as those described above, used in any setting.

Figure 2:
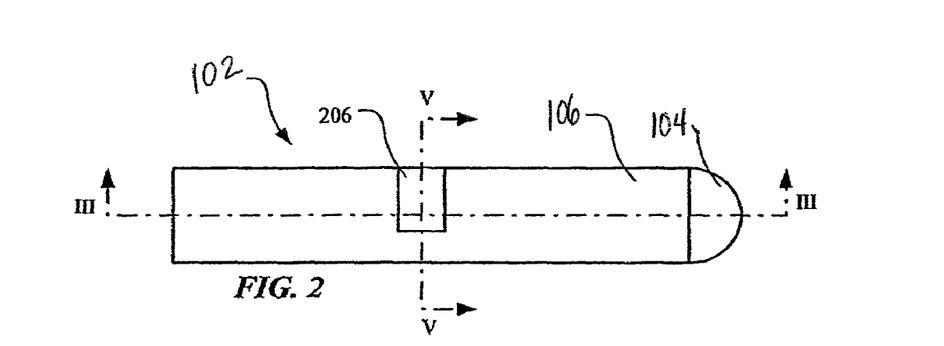
FIG. 2 is a stylized side view of a first embodiment of an electrical lead according to the present invention.
Figure 3:
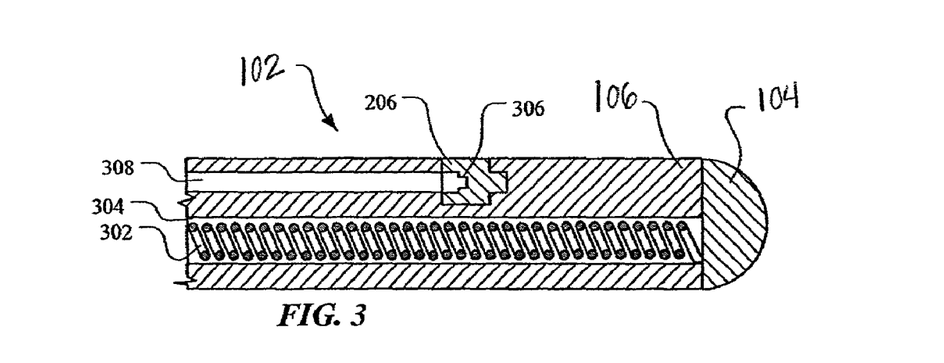
FIG. 3 is a cross-sectional view of the electrical lead of FIG. 2 taken along the III—III line in FIG. 2.

FIGS. 2–6 illustrate a first embodiment of an implantable electrical lead according to the present invention. As illustrated in FIG. 2, an elongated lead 102 includes a body 106 extending from housing portion 101 to tip electrode 104 (FIG. 1). Lead 102 may further include one or more additional electrodes, such as electrode 103 or electrode 105 of FIG. 1, or the like, for providing electrical stimuli from other points along the length of lead 102. As illustrated in FIG. 3, an electrical conductor 302 generally extends from housing portion 101 to tip electrode 104 via a lumen 304 and provides a pathway for the electrical stimuli generated by housing portion 101 to be transmitted along lead 102 and emitted through tip electrode 104. While the electrical conductor 302 is illustrated herein as a helical conductor, the scope of the present invention encompasses any desired conductor, irrespective of its shape or other characteristics.

Figure 4:
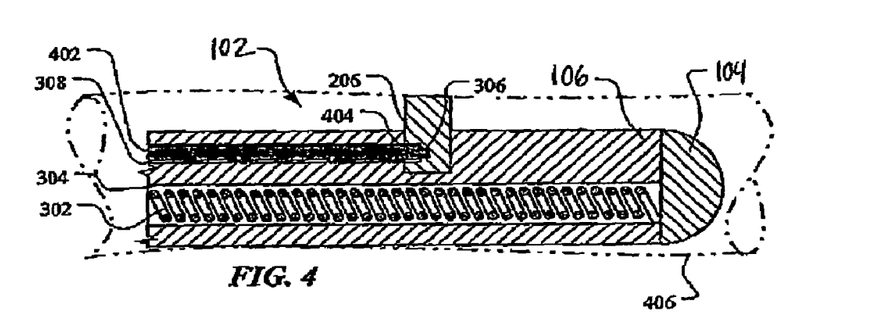
FIG. 4 is a cross-sectional view of the electrical lead of FIG. 3 with a fixation member thereof extended.

In the illustrated embodiment, lead 102 further includes a fixation member, such as a tine 206, for example, capable of being extended from elongated body 106. Tine 206 includes a fitting 306 adapted to receive a stylet 402 having a corresponding fitting 404 that is capable of mating within fitting 306 of tine 206. A lumen 308 extends from the proximal end of lead 102 (i.e., the end of lead 102 attachable to housing portion 101) to tine 206 in order for stylet 402 to be fed into lead 102 through lumen 308 so that fitting 404 of stylet 402 is mated within fitting 306 of tine 206.

Figure 6:
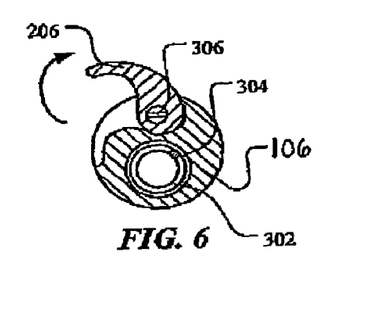
FIG. 6 is a cross-sectional view of the electrical lead of FIG. 5 with the fixation member thereof extended.
Figure 7:
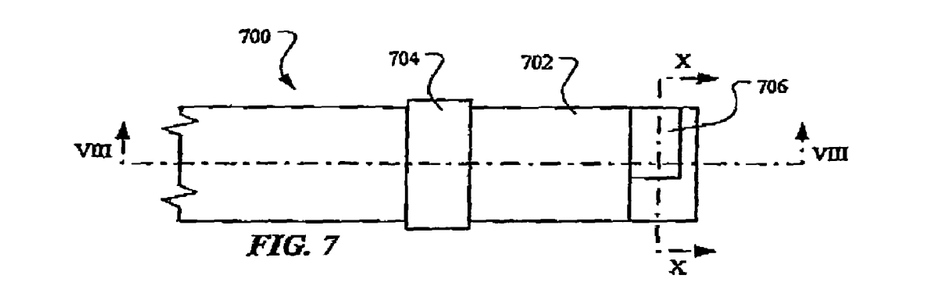
FIG. 7 is a stylized side view of a second embodiment of an electrical lead according to the present invention.

By rotating stylet 402 with respect to elongated body 106 of lead 102 while fitting 404 of stylet 402 is mated within fitting 306 of tine 206, tine 206 is rotated with respect to elongated body 106, as illustrated in FIGS. 4 and 6. As tine 206 is rotated outward, tine 206 extends from elongated body 106 to fixedly position lead 102 in place within a vessel 406 (shown in phantom), such as a coronary sinus, a cardiac vein, a coronary vein, or the like.

Figure 5:
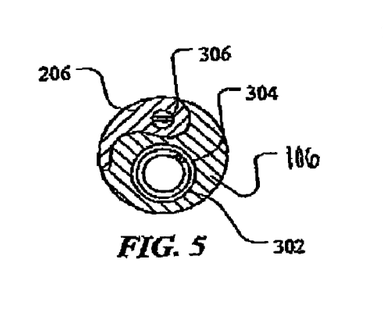
FIG. 5 is a cross-sectional view of the electrical lead of FIG. 2 taken along the V—V line in FIG. 2.

In certain circumstances, it may be desirable to remove lead 102 from vessel 406 or to reposition lead 102 within vessel 406. Accordingly, stylet 402 is fed into lumen 308 such that fitting 404 of stylet 402 is mated within fitting 306 of tine 206. Stylet 402 is then rotated to rotate tine 206 inward with respect to elongated body 106, thus retracting tine 206 toward elongated body 106 of lead 102, as illustrated in FIG. 5. Lead 200 is then removed from or repositioned within vessel 406.

It is understood that, according to the present invention, electrode 104 may be of a solid nature (stylet stops at tip of electrode 104) or of a hollow nature, allowing guide wire passage through electrode 104 for over-the-wire lead placement.

FIGS. 7–11 illustrate a second embodiment of an implantable electrical lead according to the present invention. According to the second preferred embodiment of the present invention, an electrical lead 700 includes an elongated body 702 extending from housing portion 101 (FIG. 1) to one or more ring electrodes 704. Lead 700 may also include a tip electrode, such as tip electrode 104 depicted in FIGS. 1 and 2. An electrical conductor 802 extends generally from housing portion 101 to ring electrode 704 via a lumen 804 and provides a pathway for electrical stimuli generated at housing portion and emitted by ring electrode 704. While the electrical conductor 802 is illustrated herein as a helical conductor, the scope of the present invention encompasses any one of a variety of conductors, including conductors with varying shapes or other characteristics.

Figure 8:
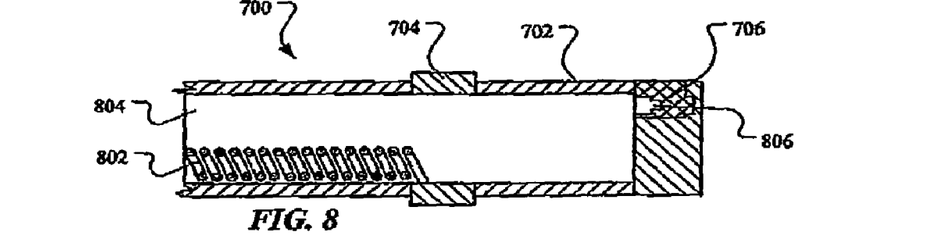
FIG. 8 is a cross-sectional view of the electrical lead of FIG. 7 taken along the VIII—VIII line in FIG. 7.
Figure 9:
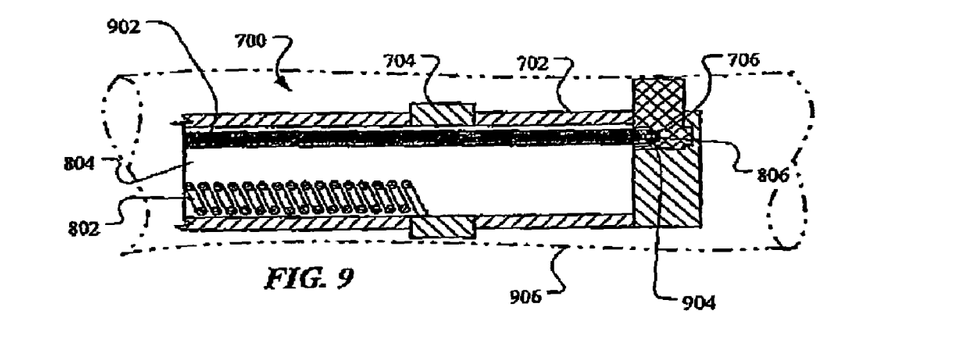
FIG. 9 is a cross-sectional view of the electrical lead of FIG. 8 depicting a fixation member thereof extended.
Figure 10:
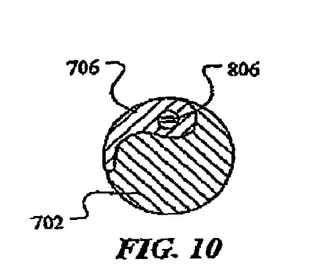
FIG. 10 is a cross-sectional view of the electrical lead of FIG. 7 taken along the X—X line in FIG. 7.

In the illustrated embodiment, lead 700 further includes a fixation member, such as a tine 706, for example, capable of being extended from elongated body 702. Tine 706 includes a fitting 806 adapted to receive a stylet 902 having a corresponding fitting 904 that is capable of mating within fitting 806 of tine 706. Stylet 902 is fed into lead 700 via lumen 804 and mated within tine 706.

Figure 11:
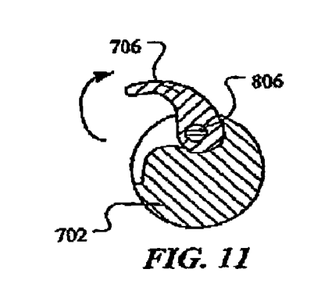
FIG. 11 is a cross-sectional view of the electrical lead of FIG. 10 depicting the fixation member thereof extended.

By rotating stylet 902 with respect to elongated body 702 while fitting 904 of stylet 902 is mated within fitting 806 of tine 706, tine 706 is rotated outward with respect to elongated body 702, as illustrated in FIGS. 9 and 11. As tine 706 is rotated, tine 706 extends outward from elongated body 702 to fixedly engage lead 700 in place within a vessel 906 (shown in phantom), such as a coronary sinus, a cardiac vein, a coronary vein, or the like.

In certain circumstances, it may be desirable to remove lead 700 from vessel 906 or to reposition lead 700 within vessel 906. Accordingly, stylet 902 is fed into lumen 804 such that fitting 904 of stylet 902 is mated within fitting 806 of tine 706. Stylet 902 is then rotated to rotate tine 706 inward with respect to elongated body 702, thus retracting tine 706 toward elongated body 702 of lead 700. Lead 700 is then removed from or repositioned within vessel 906.

In this way, the second embodiment of the present invention filters from the embodiment illustrated in FIGS. 2–6 in that tine 706 is positioned along lead 700 distal to the most distally located electrode on lead 700, i.e., electrode 704, while tine 206 is positioned along lead 102 proximal to the most distally located electrode on lead 102, i.e., electrode 104.

Figures 12, 18, 19, 20:
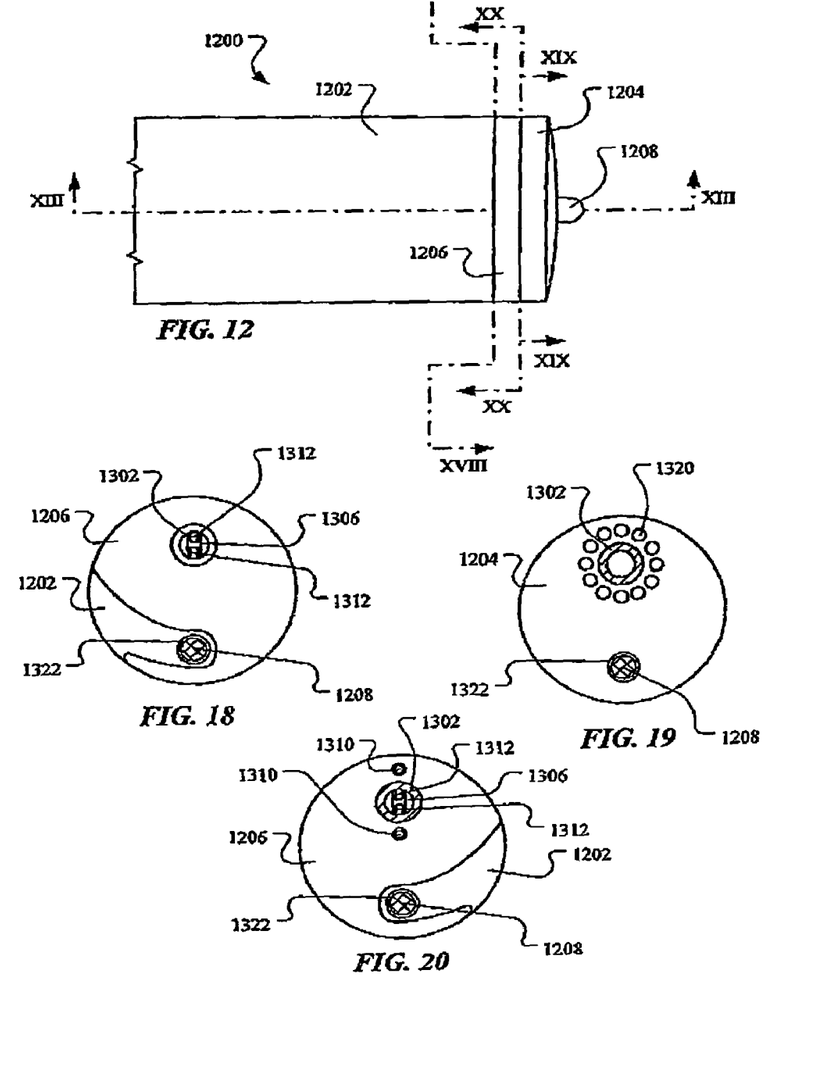
FIG. 12 is a stylized side view of a third embodiment of an electrical lead according to the present invention.
FIG. 18 is a cross-sectional view of the electrical lead of FIG. 12 taken along the XVIII—XVIII line in FIG. 12.
FIG. 19 is a cross-sectional view of the electrical lead of FIG. 12 taken along the XIX—XIX line in FIG. 12.
FIG. 20 is a cross-sectional view of the electrical lead of FIG. 12 taken along the XX—XX line in FIG. 12.

FIGS. 12–21 illustrate a third embodiment of an implantable electrical lead according to the present invention. As illustrated in FIG. 12, an electrical lead 1200 according to the present invention includes an elongated body 1202 extending from housing portion 101 (FIG. 1) to a tip electrode 1204. Lead 1200 may further include one or more additional electrodes, such as electrode 103 and electrode 105 of FIG. 1, or the like, for providing electrical stimuli from other points along the length of lead 1200.

In the illustrated embodiment of FIGS. 12–21, lead 1200 further includes a fixation member 1206 capable of being extended from the body 1202. Fixation member 1206 is rotatably attached to tip electrode 1204 by an axle 1302. Axle 1302 is fixedly attached to fixation member 1206 and is rotatably attached to tip electrode 1204. An electrical conductor 1304 extends from housing portion 101 to axle 1302 and, in combination with axle 1302, provides a pathway for the electrical stimuli generated by housing portion 101 (FIG. 1) and emitted by tip electrode 1204. While electrical conductor 1304 is illustrated herein as a helical conductor, the scope of the present invention encompasses any desired conductor, irrespective of its shape or other characteristics.

Figure 13:
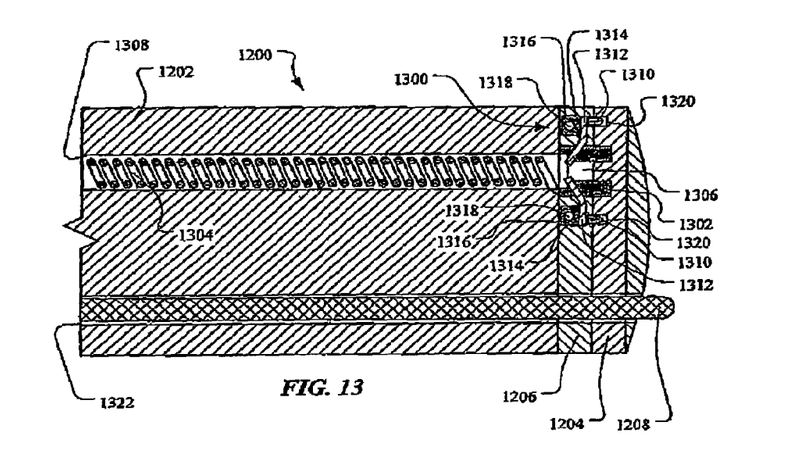
FIG. 13 is a cross-sectional view of the electrical lead of FIG. 12 taken along the XIII—XIII line in FIG. 12.
Figure 15:
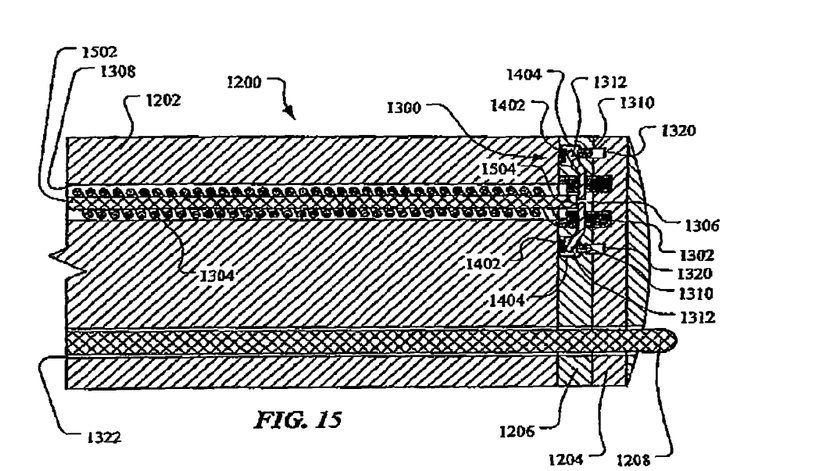
FIG. 15 is a cross-sectional view of the electrical lead of FIG. 14 depicting a release of the locking mechanism.

Axle 1302 includes a fitting 1306 adapted to receive a stylet 1502 having a fitting 1504 that is capable of mating within fitting 1306 of fixation member 1302. A lumen 1308 extends from the proximal end of lead 1200 (i.e., the end of lead 1200 attachable to housing portion 101) to fixation member 1206 so that stylet 1502 may be fed into lead 1200 and mated with fixation member 1206.

Figure 14:
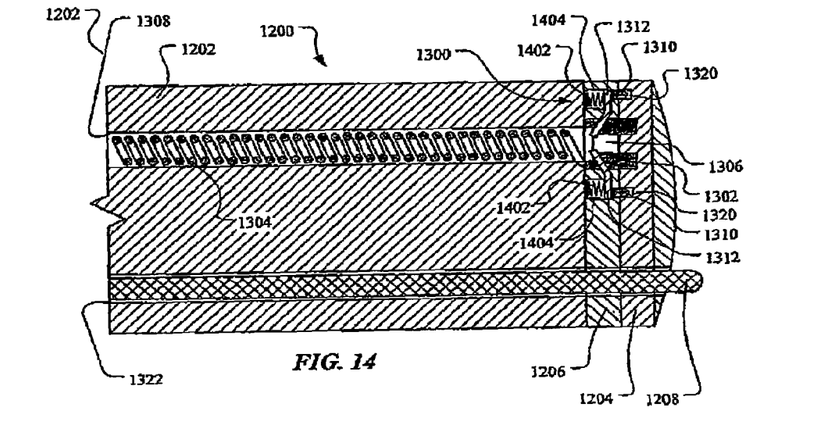
FIG. 14 is a cross-sectional view of the electrical lead of FIG. 13 depicting an alternate spring configuration for a locking mechanism.

Lead 1200 further includes a locking mechanism 1300 for holding fixation member 1206 in a particular orientation with respect to elongated body 1202. Locking mechanism 1300 includes one or more pins 1310 (two pins 1310 in the illustrated embodiment) that are held in an extended position by a corresponding number of springs disposed within fixation member 1206. A lever 1312 is disposed between each of the springs and pins 1310. In one embodiment, illustrated in FIG. 13, the springs include bladders 1314 containing silicone oil 1316. An air bubble 1318 is disposed within silicone oil 1316. Alternatively, the springs are helical springs 1402 disposed within bores 1404 in fixation member 1206. Other desired embodiments and variations of the springs disclosed herein are considered within the scope of the present invention.

Figure 16:
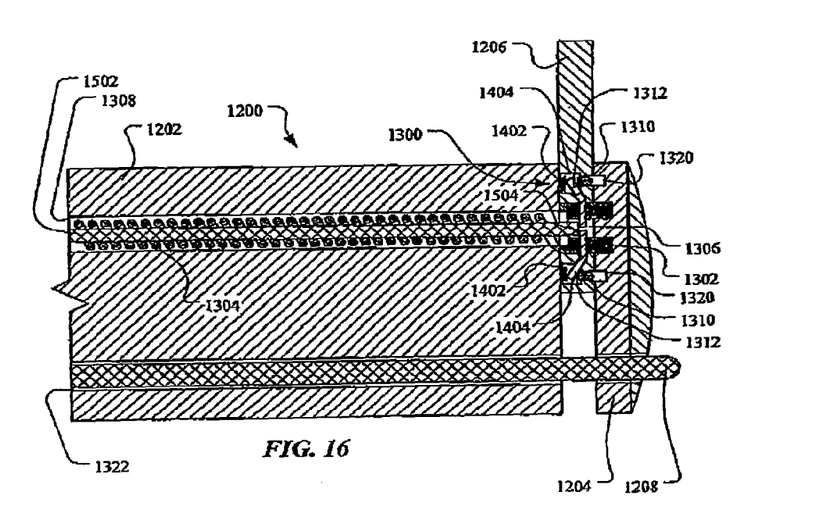
FIG. 16 is a cross-sectional view of the electrical lead of FIG. 14 depicting a fixation member thereof extended with the locking mechanism released.
Figures 17, 21:
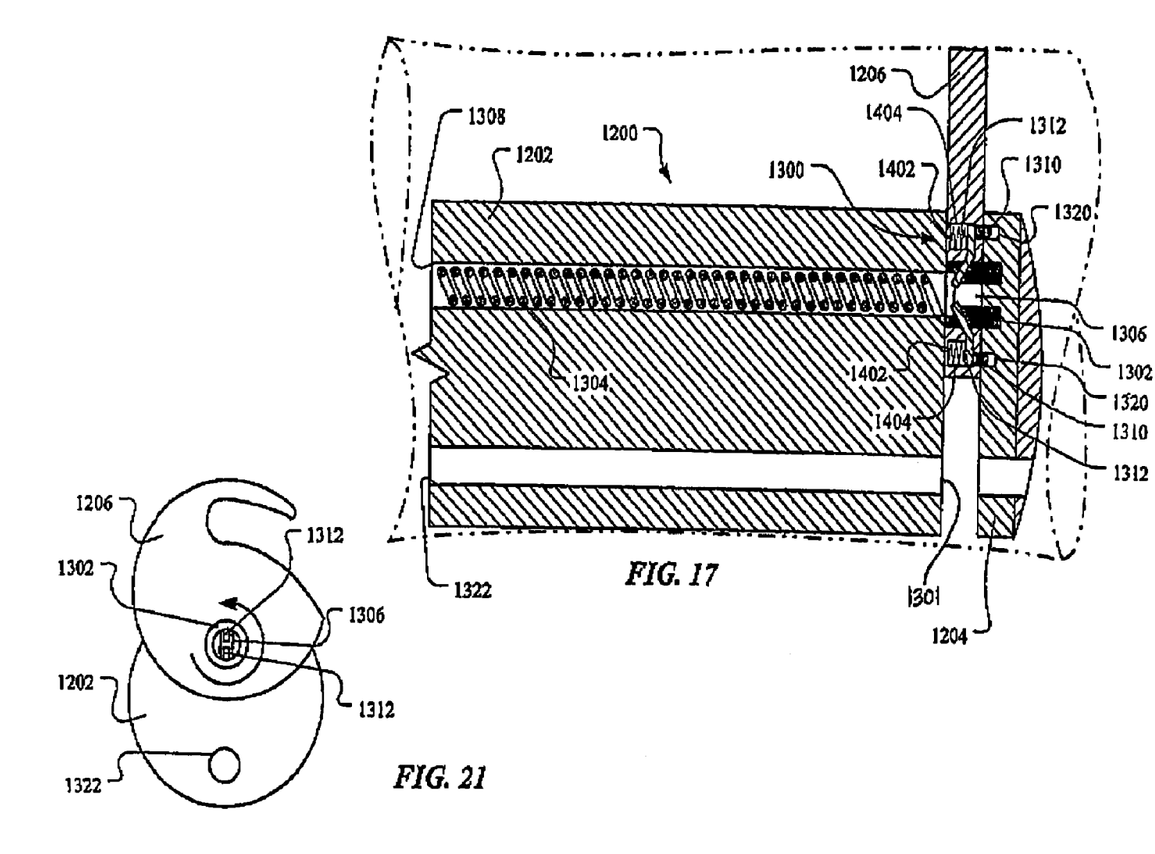
FIG. 17 is a cross-sectional view of the electrical lead of FIG. 14 depicting the fixation member thereof extended with the locking mechanism engaged.
FIG. 21 is a cross-sectional view of the electrical lead of FIG. 18 depicting the fixation member thereof extended.
Figure 22:
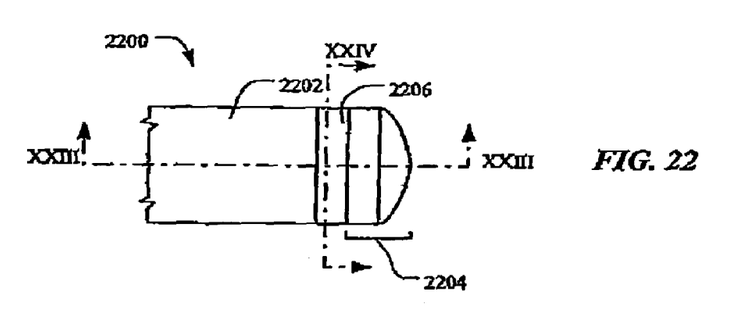
FIG. 22 is a stylized side view of a fourth embodiment of an electrical lead according to the present invention.

Locking mechanism 1300 further includes a plurality of bores 1320 spaced radially from and concentric with axle 1302. Referring to FIG. 15, as stylet 1502 is fed through lumen 1308, stylet 1502 contacts levers 1312. As stylet 1502 is urged further into lumen 1308, levers 1312 compress the springs (e.g., bladders 1314, helical springs 1402, or the like), which retract pins 1310 from bores 1320 and allows fitting 1504 of stylet 1502 to mate within fitting 1306 of axle 1302. While maintaining pressure on stylet 1502 (and thus levers 1312), stylet 1502 is rotated to thus rotate axle 1302 to rotate fixation member 1206 outward to the desired position, as illustrated in FIG. 16. Upon releasing pressure on stylet 1502 (and thus levers 1312), the springs (e.g., bladders 1314, helical springs 1402, or the like) urge levers 1312 to their original position and urge pins 1310 into matching bores 1320, thereby locking fixation member 1206 in an outward position relative to elongated body 1202, as illustrated in FIGS. 16–18. Lead 1200 is now fixedly engaged within a vessel 1702.

Alternatively, stylet 1502 may be used only to transmit pressure to levers 1312. In such an embodiment, electrical conductor 1304 is rotated to effect rotation of fixation member 1302.

In the same way, while maintaining pressure on stylet 1502 (and thus levers 1312), stylet 1502 is rotated to thus rotate axle 1302 and fixation member 1206 to the desired inward position, as illustrated in FIG. 15. Upon releasing pressure on stylet 1502 (and thus levers 1312), the springs (e.g., bladders 1314, helical springs 1402, or the like) urge levers 1312 to their original position and urge pins 1310 into matching bores 1320, thereby locking fixation member 1206 in an inward position relative to elongated body 1202, as illustrated in FIGS. 13–15. Lead 1200 is then removed from or repositioned within vessel 1702.

The illustrated embodiment further includes a guide wire lumen 1322. In one embodiment, a guide wire 1208 is fed into vessel 1702, such as a coronary sinus, a cardiac vein, a coronary vein, or the like, wherein the lead is to be placed. Lead 1200 is then guided over guide wire 1208 by passing guide wire 1208 through guide wire lumen 1322 until lead 1200 is in the desired location within vessel 1702. While the illustrated embodiment includes a guide wire lumen 1322 for use with a guide wire 1208, the scope of the present invention encompasses a lead that omits guide wire lumen 1322. A seal, such as a silicone rubber seal, for example, may be positioned at an opening 1301 at end of lumen 1322 to prevent ingress of fluids within lumen 1322 when fixation member 1206 of lead 1200 is in the open, extended position within the vessel.

FIGS. 22–26 illustrate a fourth embodiment of the present invention. A lead 2200 includes an elongated body 2202 extending from housing portion 101 (FIG. 1) to a distal portion 2204 of lead 2200. Distal portion 2204 may, in one embodiment, be a tip electrode such as the tip electrode 104 of FIG. 1. Lead 2200 may further include one or more additional electrodes, such as electrode 103 and electrode 105 of FIG. 1, or the like, for providing electrical stimuli from other points along the length of lead 2200.

Figure 23:
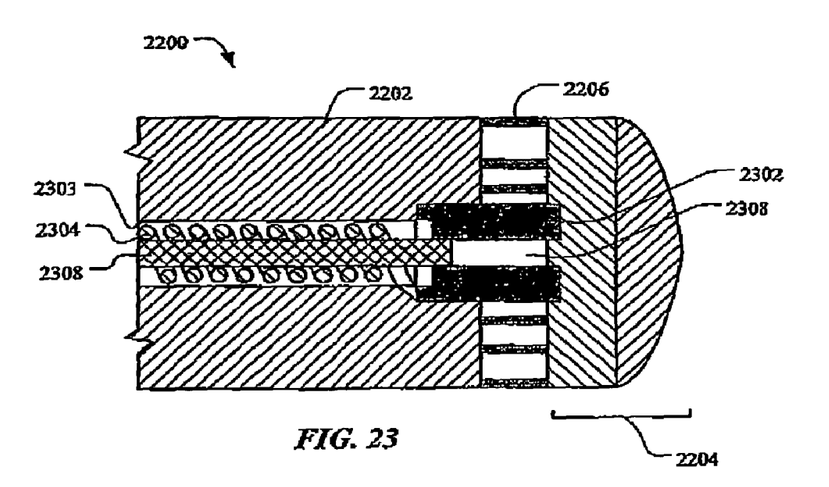
FIG. 23 is a cross-sectional view of the electrical lead of FIG. 22 taken along the XXIII—XXIII line in FIG. 22.
Figure 24:
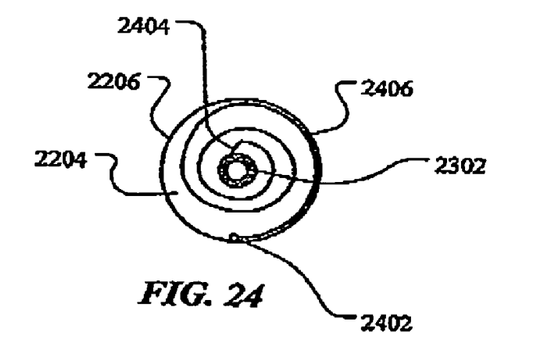
FIG. 24 is a cross-sectional view of the electrical lead of FIG. 22 taken along the XXIV—XXIV line in FIG. 22.

In the illustrated embodiment, the lead 2200 further includes a fixation member, such as a coil 2206 that is capable of being extended from elongated body 1202 and also acts as an electrode. As illustrated in FIGS. 23 and 24, a first end 2402 of coil 2206 is affixed to elongated body 2202 and/or distal portion 2204 of lead body 2202 and a second end 2404 of coil 2206 is affixed to an axle 2302. Axle 2302 is rotatably attached to elongated body 2202 and distal portion 2204 of lead 2200. Electrical conductor 2304 extends from housing portion 101 to axle 2302 via a lumen 2303 and, in combination with axle 2302, provides a pathway for the electrical stimuli generated by housing portion 101 and emitted by the coil. While electrical conductor 2304 is illustrated herein as a helical conductor, the scope of the present invention encompasses any desired conductor, irrespective of its shape or other characteristics.

Figure 25:
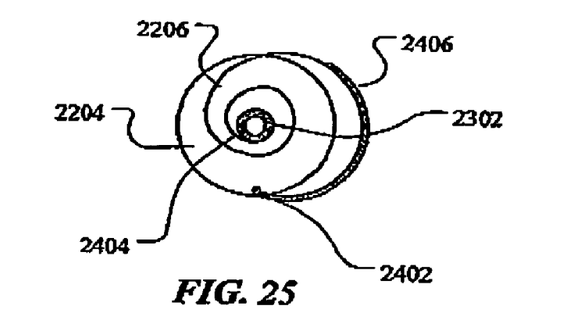
FIG. 25 is a cross-sectional view of the electrical lead of FIG. 24 depicting a fixation member thereof extended.
Figure 26:
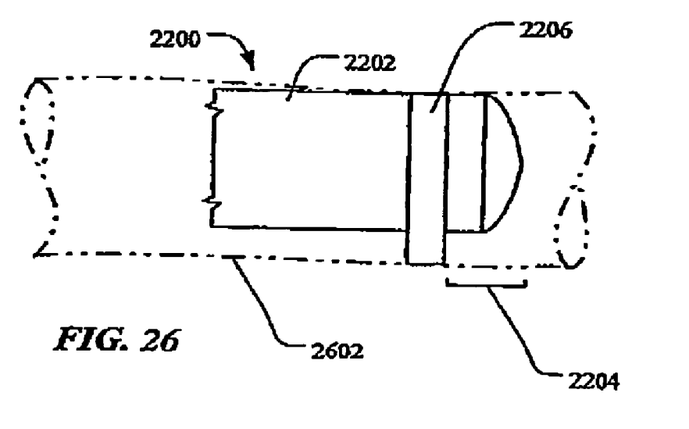
FIG. 26 is a stylized side view of the electrical lead of FIG. 22 depicting the fixation member thereof extended.

The axle 2302 includes a fitting 2306 adapted to receive a stylet 2308 having a fitting 2310 that is capable of mating within fitting 2306 of axle 2302. Stylet 2308 is fed into lead 2200 via lumen 2303 and mated with axle 2302. In one embodiment the lead includes a locking mechanism corresponding to locking mechanism 1300, first depicted in FIG. 13. Thus, as stylet 2308 is rotated with respect to lead 2202, coil 2206 is unwound and extends outward from body 2202, as illustrated in FIGS. 25 and 26. Coil 2206 may be rewound and retracted radially inward toward body 2202 by counter-rotating axle 2302 via stylet 2308.

Alternatively, electrical conductor 2304 is rotated to effect radial extension of coil 2206. Further, in the illustrated embodiment, a portion of coil 2206 is covered with a porous, metallic layer 2406 to improve conduction of the electrical stimuli to vessel 2602. The scope of the present invention encompasses the inclusion of such metallic layers to any of the electrode surfaces disclosed herein. In addition, a seal, such as a silicone rubber seal, for example, is positioned on a portion of coil 2206 to prevent ingress of fluids when coil 2206 is in the retracted position, while providing a smooth surface on the outer surface of lead 2202 while coil 2206 is in the retracted position. According to an alternate embodiment of the present invention, the silicone seal may be located along the outer walls of lead 2202 so as to engage against coil 2206 when coil 2206 is in the retracted position.

While the embodiments illustrated herein provide fittings (e.g., fittings 306, 404, 806, 904, 1306, 1504, 2306, 2310) of a particular configuration, the scope of the present invention encompasses fittings of any desired configuration. For example, the fittings may be mating blade-type, hexagonal, cruciform, square, Torx®, or the like fittings.

Figure 27:
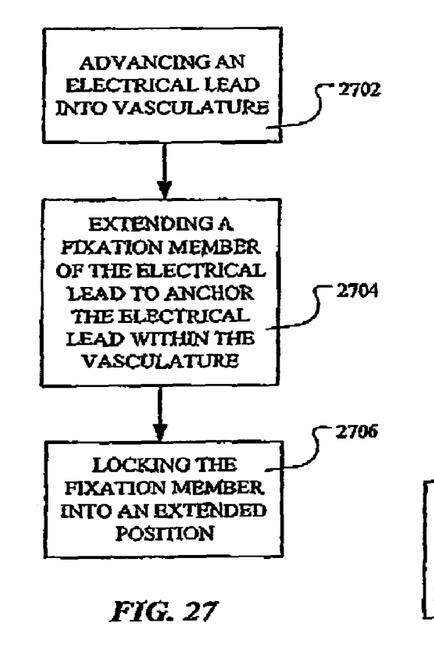
FIG. 27 is a flow chart depicting a method for installing and fixedly engaging an electrical lead according to the present invention.

FIG. 27 illustrates a method for installing and fixedly engaging an electrical lead according to the present invention. The method includes advancing an electrical lead into vasculature, such as a coronary sinus, a cardiac vein, a coronary vein, or the like (block 2702) and extending a fixation member of the electrical lead to fixedly engage the electrical lead within the vasculature (block 2704). The fixation member may be extended by advancing a stylet into the electrical lead, engaging the stylet with the fixation member, and rotating the stylet such that the fixation member is extended. Alternatively, the fixation member may be extended by rotating an electrical conductor coupled with the fixation member. The electrical lead may be advanced into the vasculature by advancing a guide wire into the vasculature and advancing the electrical lead into the vasculature by passing the guide wire through a guide wire lumen in the electrical lead. Alternatively, the electrical lead may be advanced into the vasculature alone. In one embodiment, the method further includes locking the fixation member into an extended position (block 2706).

Figure 28:
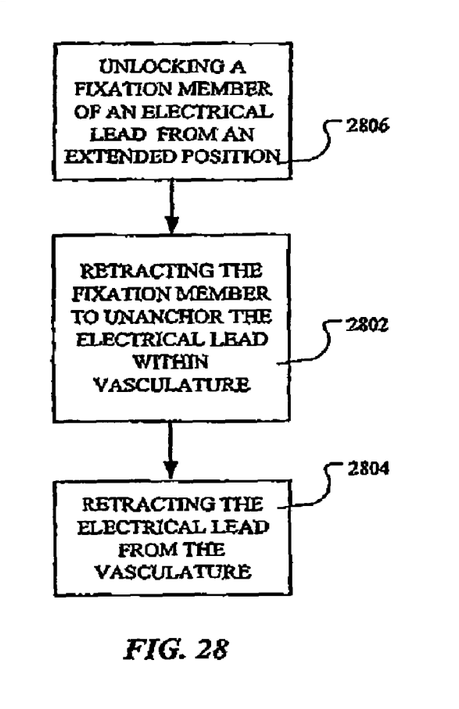
FIG. 28 is a flow chart depicting a method for disengaging and uninstalling an electrical lead according to the present invention.

FIG. 28 illustrates a method for disengaging and uninstalling an electrical lead according to the present invention. The method includes retracting a fixation member to disengage the electrical lead within vasculature (block 2802) and retracting the electrical lead from the vasculature (block 2804). The fixation member may be retracted by advancing a stylet into the electrical lead, engaging the stylet with the fixation member, and rotating the stylet such that the fixation member is retracted. Alternatively, the fixation member may be retracted by rotating an electrical conductor coupled with the fixation member. In one embodiment, the method further includes unlocking the fixation member from an extended position (block 2806).

While certain embodiments disclosed herein are designed to be used with a guide wire and others are not, the scope of the present invention encompasses each of the disclosed embodiments, and their equivalents, modified to be used either with a guide wire or without a guide wire.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A lead of an implantable medical device, comprising:
   an elongated body having a proximal end;
   a fixation member joined to the elongated body and distally disposed from the proximal end of the elongated body, wherein the fixation member is capable of being extended radially outward from and retracted inward toward the elongated body to provide fixation of a distal part of the elongated body within a portion of a great coronary vein of a subject:
   a locking mechanism for selectively restricting the fixation member from being extended radially outward from and retracted radially inward toward the elongated body, the locking mechanism comprising:
   a pin disposed in the fixation member;
   a plurality of bores disposed in the elongated body such that, as the fixation member is extended outward from and retracted inward toward the elongated body, the pin is capable of slidingly engaging one of the plurality of bores;

a spring disposed in the fixation member; and a lever disposed between the spring and the pin such that, as the lever is moved in a first direction, the spring is compressed and the pin is retracted from the bore and, as the lever is moved in a second direction opposite to the first direction, the spring is uncompressed and the pin is extended into the bore.

2. A lead, according to claim 1, further comprising:

a stylet member;

a fitting located within the fixation member capable of mating with the stylet; and a lumen, positioned in the elongated body, extending from the proximal end of the elongated body to the fittng of the fixation member, wherein the stylet is fed through the lumen and mated with the fitting of the fixation member.

3. A lead, according to claim 1, further comprising an electrical conductor extending from the proximal end to the fixation member, wherein the electrical conductor is capable of being used to extend the fixation member.

4. A lead, according to claim 1, wherein the elongated body includes a distal end and the fixation member is disposed proximate the distal end.

5. A lead, according to claim 1, further comprising a conductor extending within the elongated body and electrically coupled with the fixation member such that electrical stimuli may be transmitted through the conductor and emitted by the fixation member.

6. A lead, according to claim 1, further comprising a bladder positioned in the spring, the bladder containing silicone oil and having an air bubble disposed within the silicone oil.

7. A lead, according to claim 1, further comprising:

a stylet insertable within a lumen of the lead;

a fitting, positioned within the fixation member, capable of mating with the stylet; and a lumen extending from the proximal end of the elongated body to the fitting of the fixation member such that the stylet is fed through the lumen to move the lever and mate with the filling of the fixation member.

8. A lead, according to claim 1, further comprising a guide wire lumen positioned within the elongated body.

9. A lead, according to claim 1, further comprising:

an axle joining a proximal portion of the elongated body and a distal portion of the elongated body; and a coil located in the fixation member, the coil having a first end joined to at least one of the proximate portion and the distal portion and a second end joined to the axle such that, as the axle is rotated, the coil is extended radially outward from and retracted radially inward toward the elongated body.

10. A lead, according to claim 9, wherein a porous, metallic layer is disposed on at least a portion of the coil.

* * * * *

UNITED STATES PATENT AND TRADEMARK OFFICE
CERTIFICATE OF CORRECTION

| | |
|---|---|
| PATENT NO. | : 7,076,309 B2 |
| APPLICATION NO. | : 10/137466 |
| DATED | : July 11, 2006 |
| INVENTOR(S) | : Douglas S. Hine et al. |

It is certified that error appears in the above-identified patent and that said Letters Patent is hereby corrected as shown below:

Col. 8, line 60, please delete "a subject:" and insert --a subject;--.

Col. 10, line 14, please delete "the filling" and insert --the fitting--.

Signed and Sealed this

Second Day of January, 2007

JON W. DUDAS
*Director of the United States Patent and Trademark Office*